US006720177B2

United States Patent
Ghadiri et al.

(10) Patent No.: US 6,720,177 B2
(45) Date of Patent: Apr. 13, 2004

(54) POROUS SEMICONDUCTOR-BASED OPTICAL INTERFEROMETRIC SENSOR

(75) Inventors: M. Reza Ghadiri, San Diego, CA (US); Michael J. Sailor, LaJolla, CA (US); Kianoush Motesharei, La Jolla, CA (US); Shang-Yi Lin, San Diego, CA (US); Keiki-Pua S. Dancil, Del Mar, CA (US)

(73) Assignees: The Regents of the University of California, San Diego, CA (US); The Scripps Research Institute, La Jolla, CA (US)

( * ) Notice: Subject to any disclaimer, the term of this patent is extended or adjusted under 35 U.S.C. 154(b) by 155 days.

(21) Appl. No.: 09/795,533

(22) Filed: Feb. 28, 2001

(65) Prior Publication Data

US 2001/0044119 A1 Nov. 22, 2001

Related U.S. Application Data

(60) Division of application No. 08/961,308, filed on Oct. 30, 1997, now Pat. No. 6,248,539, which is a continuation-in-part of application No. 08/924,601, filed on Sep. 5, 1997, now abandoned.

(51) Int. Cl.⁷ .............................................. G01N 33/543
(52) U.S. Cl. .................... 435/287.1; 356/345; 356/352; 385/12; 385/129; 385/130; 422/82.05; 422/82.11; 435/287.2; 435/288.7; 435/808; 435/973; 435/7.1; 436/164; 436/165; 436/518; 436/524; 436/527; 436/805
(58) Field of Search ................................ 356/345, 352; 385/12, 129, 130; 422/82.05, 82.11; 435/287.1, 287.2, 288.7, 808, 973, 7.1; 436/164, 165, 518, 524, 527, 805

(56) References Cited

U.S. PATENT DOCUMENTS

| | | | | |
|---|---|---|---|---|
| 4,521,522 A | * | 6/1985 | Lundstrom et al. | 436/525 |
| 4,558,012 A | * | 12/1985 | Nygren et al. | 436/518 |
| 4,828,986 A | | 5/1989 | Smith et al. | 435/7 |
| 4,833,093 A | * | 5/1989 | Malmqvist et al. | 436/527 |
| 5,077,210 A | * | 12/1991 | Eigler et al. | 435/176 |
| RE33,897 E | | 4/1992 | Vaughan et al. | 530/326 |
| 5,281,710 A | | 1/1994 | Smith et al. | 546/18 |
| 5,338,415 A | | 8/1994 | Sailor et al. | 204/129 |
| 5,418,136 A | * | 5/1995 | Miller et al. | 435/5 |
| 5,804,453 A | * | 9/1998 | Chen | 435/176 |

OTHER PUBLICATIONS

Wood, *Microchemical Journal*, 47:330–337 (1993).
DeRisi et al., *Nature Genetics*, 14:457–460 (1996).
Ferguson et al. *Nature Biotechnology*, 14:1681–1684 (1996).
Southern et al., *Nucleic Acids Research*, 22(8):1368–1373 (1994).
Lee et al., *J. Am. Chem. Soc.*, 118:5375–5382 (1996).
Curtis et al., *J. Electrochem. Soc.* 140:3492 (1993).
Piehler et al., *Biosensors & Bioelectronics*, 11(6/7):579–590 (1996).

(List continued on next page.)

Primary Examiner—Christopher L. Chin
(74) Attorney, Agent, or Firm—Welsh & Katz, Ltd.

(57) ABSTRACT

The measurement of the wavelength shifts in the reflectometric interference spectra of a porous semiconductor substrate such as silicon, make possible the highly sensitive detection, identification and quantification of small analyte molecules. The sensor of the subject invention is effective in detecting multiple layers of biomolecular interactions, termed "cascade sensing", including sensitive detection of small molecule recognition events that take place relatively far from the semiconductor surface.

6 Claims, 4 Drawing Sheets

OTHER PUBLICATIONS

Lee et al., *J. Vac. Sci. Technol. B*, 14(4):2850–2854 (1996).
Doan et al., *Science*, 256:1791–1792 (1992).
Lee et al., *J. Am. Chem. Soc.*, 117:8295–8296.
Chee et al., *Science*, 274:610–614 (1996).
Shoemaker et al., *Nature Genetics*, 14:450–456 (1996).
Stayton et al., *Nature*, 378:472–474 (1995).
Barnard et al., *Science*, 251:927–929 (1991).
Hatfield et al., *Sensors and Actuators B*, 18–19:221–228 (1994).
Jost et al., *Nucleic Acids Research*, 19(10):2788 (1991).
Watanabe et al., *Sensors and Actuators B*, 33:194–197 (1996).
Ben–Chorin et al., *Appl. Phys. Lett.*, 64(4):481–483 (1994).
Heinrich et al., *Appl. Phys. Lett.*, 48(16):1066–1068 (1986).
Shurmer et al., *Sensors and Actuators B*, 4:29–33 (1991).
Stievenard et al., *Appl. Phys. Lett.*, 67(11):1570–1572 (1995).
Rowell, *Biochemical Society Transactions*, 19:32–35 (1991).
Yim et al., *Biosensors & Bioelectronics*, 8:1–38 (1993).
Shinohara et al., *J. Biochem.*, 117(5):1076–1082 (1995).
Meyer et al., *J. Am. Chem. Soc.*, 110:4914–4918 (1988).
Ingenhoff et al., *Fresenius J. Anal. Chem.*, 346:580–583 (1993).
Brecht et al., *Analusis*, 20:135–140 (1992).
Gauglitz et al., *Sensors and Actuators B*, 11:21–27 (1993).
Bernard et al., *Eur. J. Biochem.*, 230:416–423 (1995).
Parthasarathy et al., *Nature*, 369:298–301 (1994).
Riklin et al., *Nature*, 376:672–675 (1995).
Laurell et al., *Sensors and Actuators B*, 31:161–166 (1996).
Frew et al., *Analytical Chemistry*, 59(15):933–944 (1987).
Hutchinson, *Analytical Biochemistry*, 220:303–307 (1994).
Shinohara et al., *Eur. J. Biochem.*, 223:189–194 (1994).
Hickman et al., *Science*, 252:688–691 (1991).
Hafeman et al., *Science*, 420:1182–1185 (1988).
Iwamoto et al., *Nature*, 353:645–647 (1991).
Dickinson et al., *Nature*, 382:697–700 (1996).
Yamanaka et al., *J. Am. Chem. Soc.* 117:9095–9096 (1995).
King et al., *Science*, 249: 778–781 (1990).
Brecht et al., *Biosensors & Bioelectronics*, 10:923–936 (1995).
Clerc et al., *Sensors and Actuators B*, 11:461–465 (1993).
McConnell et al., *Science,* 257: 1906–1912 (1992).
Piehler et al., *Analytical Chemistry*, 68(1):139–143 (1996).
Meyer et al., *J. Am. Chem. Soc.*, 111:5146–5148 (1989).
Brecht et al., *Biosensors & Bioelectronics*, 8:387–392 (1993).
Brecht et al., *Frontiers in Biosensorics II*, 81:1–16 (1997).
Spinke et al., *Langmuir*, 9:1821–1825 (1993).

* cited by examiner

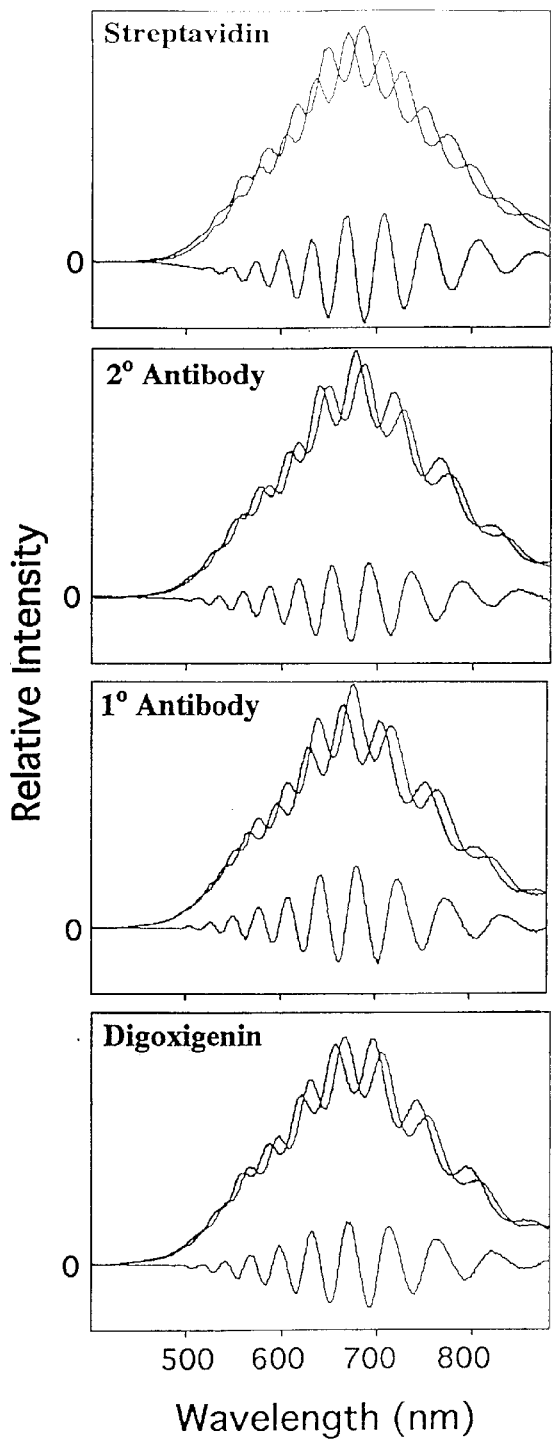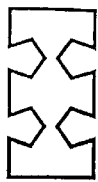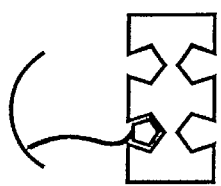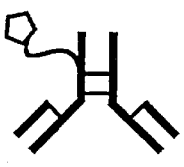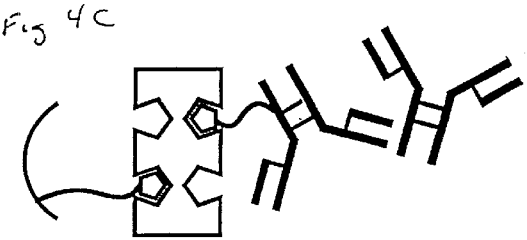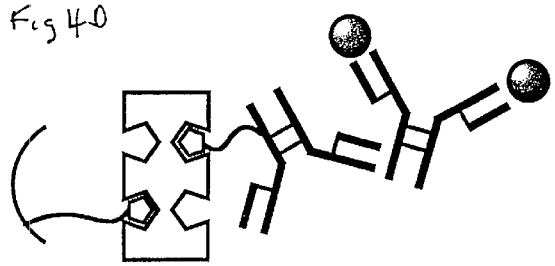
Fig 4A
Fig 4B
Fig 4C
Fig 4D

SEQUENCE LISTING

<160> NUMBER OF SEQ ID NOS: 5

<210> SEQ ID NO 1
<211> LENGTH: 16
<212> TYPE: DNA
<213> ORGANISM: artificial sequence
<220> FEATURE:
<223> OTHER INFORMATION: oligonucleotide

<400> SEQUENCE: 1
gccagaaccc agtagt                                                 16

<210> SEQ ID NO 2
<211> LENGTH: 16
<212> TYPE: DNA
<213> ORGANISM: artificial sequence
<220> FEATURE:
<223> OTHER INFORMATION: oligonucleotide

<400> SEQUENCE: 2
ccggacagaa gcagaa                                                 16

<210> SEQ ID NO 3
<211> LENGTH: 16
<212> TYPE: DNA
<213> ORGANISM: artificial sequence
<220> FEATURE:
<223> OTHER INFORMATION: Complementary strand of seq. id no. 1

<400> SEQUENCE: 3
actactgggt tctggc                                                 16

-continued

```
<210> SEQ ID NO 4
<211> LENGTH: 16
<212> TYPE: DNA
<213> ORGANISM: artificial sequence
<220> FEATURE:
<223> OTHER INFORMATION: Complementary strand of seq. id. no. 2

<400> SEQUENCE: 4
ttctgcttct gtccgg                                                    16

<210> SEQ ID NO 5
<211> LENGTH: 20
<212> TYPE: PRT
<213> ORGANISM: artificial sequence
<220> FEATURE:
<223> OTHER INFORMATION: synthetic polypeptide related to Epstein-Barr
      virus nuclear antigen

<400> SEQUENCE: 5

Ala Gly Ala Gly Gly Gly Ala Gly Gly Ala Gly Ala Gly Gly Gly Ala
1               5                   10                  15

Gly Gly Ala Gly
            20
```

POROUS SEMICONDUCTOR-BASED OPTICAL INTERFEROMETRIC SENSOR

CROSS-REFERENCE TO RELATED APPLICATION

This is a divisional of application Ser. No. 08/961,308, filed Oct. 30, 1997 now U.S. Pat. No. 6,248,539, which is a continuation-in-part of application Ser. No. 08/924,601, filed Sep. 5, 1997, now abandoned.

TECHNICAL FIELD

This invention is related to solid state sensors and, more particularly, to the use and preparation of a porous semiconductor such as a silicon wafer for the quantitative and qualitative analysis of an analyte such as an organic analyte.

BACKGROUND OF THE INVENTION

Solid-state sensors and particularly biosensors have received considerable attention lately due to their increasing utility in chemical, biological, and pharmaceutical research as well as disease diagnostics. In general, biosensors consist of two components: a highly specific recognition element and a transducing structure that converts the molecular recognition event into a quantifiable signal. Biosensors have been developed to detect a variety of biomolecular complexes including oligonucleotide pairs, antibody-antigen, hormone-receptor, enzyme-substrate and lectin-glycoprotein interactions. Signal transductions are generally accomplished with electrochemical, field-effect transistor, optical absorption, fluorescence or interferometric devices.

It is known that the intensity of the visible photoluminescence changes of a porous silicon film depend on the types of gases adsorbed to its surface. Based on this phenomenon, a simple and inexpensive chemical sensor device was developed and disclosed in U.S. Pat. No. 5,338,415.

As disclosed in that patent, porous films of porous films of silicon (Si) can be fabricated that display well-resolved Fabry-Perot fringes in their optical reflectance properties. The production of a porous silicon (Si) layer that is optically uniform enough to exhibit these properties may be important for the design of etalons (thin film optical interference devices for laser spectroscopy applications) and other optical components utilizing porous Si wafers. Such interference-based spectra are sensitive to gases or liquids adsorbed to the inner surfaces of the porous Si layer.

Ever increasing attention is being paid to detection and analysis of low concentrations of analytes in various biologic and organic environments. Qualitative analysis of such analytes is generally limited to the higher concentration levels, whereas quantitative analysis usually requires labeling with a radioisotope or fluorescent reagent. Such procedures are time consuming and inconvenient. Thus, it would be extremely beneficial to have a quick and simple means of qualitatively and quantitatively detect analytes at low concentration levels. The invention described hereinafter provides one such means.

BRIEF SUMMARY OF THE INVENTION

The subject invention contemplates the detection and, if desired, measurement of the wavelength shifts in the reflectometric interference spectra of a porous semiconductor substrate such as a silicon substrate that make possible the highly sensitive detection, identification and quantification of small molecules and particularly, small organic molecules (i.e., carbon-containing molecules e.g., biotin, and the steroid digoxigenin), short DNA oligonucleotides (e.g., 16-mers), and proteins (e.g., streptavidin and antibodies). The binding of inorganic species such as metal ions is also contemplated. Most notably, the sensor of the subject invention has been shown to be highly effective in detecting multiple layers of biomolecular interactions, termed "cascade sensing", including sensitive detection of small molecule recognition events that take place relatively far from the silicon surface.

In an exemplary embodiment, a p-type silicon (Si) wafer (substrate) is galvanostatically etched in a hydrofluoric acid (HF)-containing solution. The etched wafer is rinsed with ethanol and dried under a stream of nitrogen gas. Reflection of white light off the porous silicon results in an interference pattern that is related to the effective optical thickness. The binding of an analyte to a recognition partner immobilized in the porous silicon substrate results in a change in the refractive index, which is detected as a wavelength shift in the reflection interference pattern.

One benefit of the present invention is the provision of a device for detecting the presence of target (analyte) molecules such as biological or organic compound molecules at very low concentrations.

An advantage of the present invention is the provision of a means for detecting the presence of multilayered molecular assemblies.

Still another benefit of the present invention is a device that is capable of quantitatively detecting an analyte.

Still another advantage of the present invention is that the presence of an analyte in a sample solution can often be detected by visual inspection, and without the need for special apparatus.

Still further benefits and advantages will be apparent to a worker of ordinary skill from the disclosure that follows.

BRIEF DESCRIPTION OF THE DRAWINGS

An understanding of the present invention will be facilitated by consideration of the following detailed description of a preferred embodiment of the present invention, taken in conjunction with the accompanying drawings, in which like reference numerals refer to like parts and in which:

FIGS. 4A, 4B, 4C and 4D are cascade sensing and reflectometric interference spectra of multilayered molecular assemblies.

DETAILED DESCRIPTION OF THE INVENTION

Figure 1:
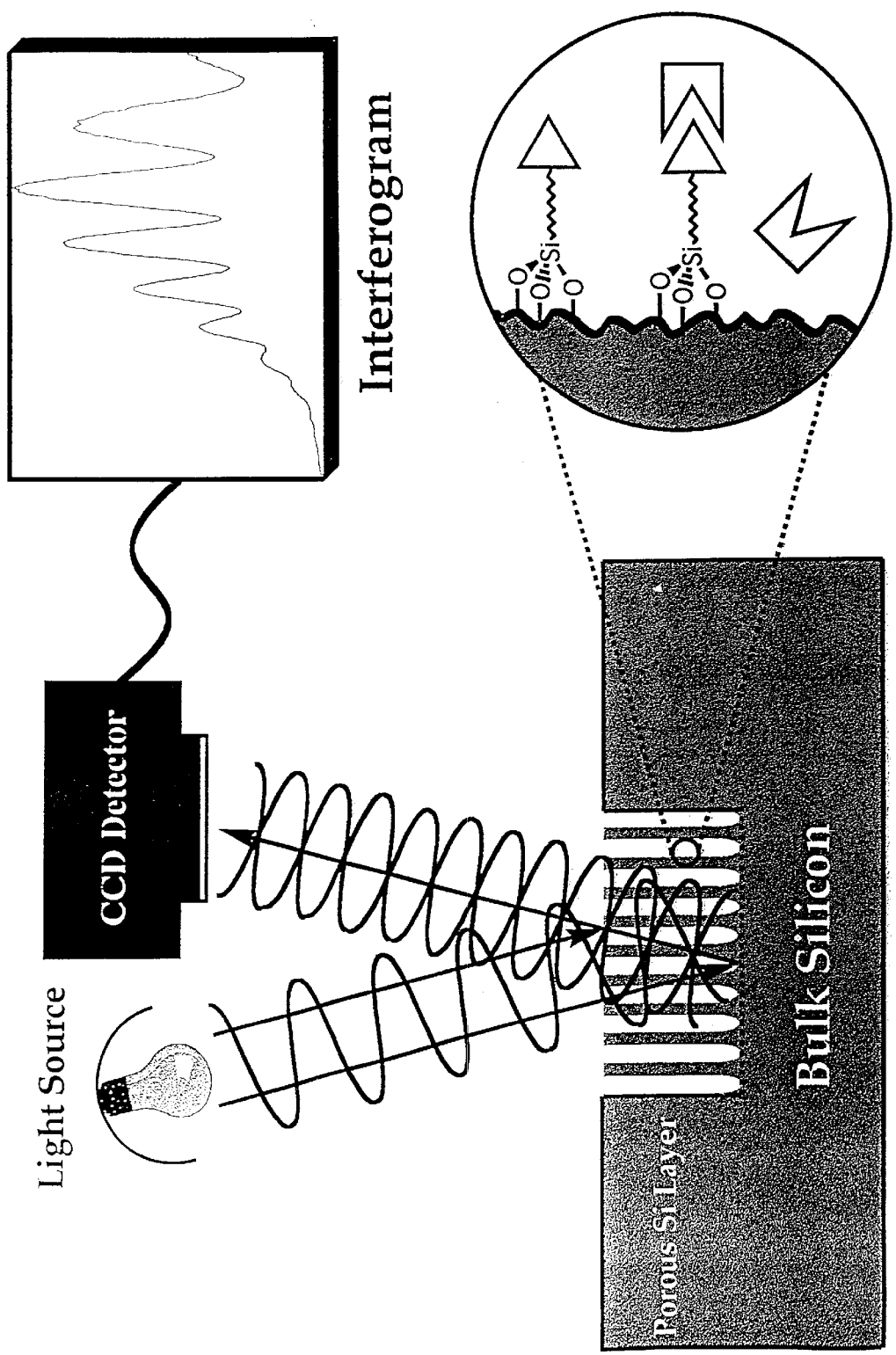
FIG. 1 is a schematic representation of the porous semiconductor, e.g., silicon-based optical interferometric biosensor of the present invention.

A contemplated interferometric sensor is depicted in FIG. 1 and is extremely sensitive in detecting the presence of a number of ligands (analytes) that bind specifically to a chemical binder on the sensor surface. For example, the lowest DNA concentration measured with a contemplated porous Si interferometric sensor was 9 $fg/mm^2$. For comparison, the detection limits of current technologies are: Interferometry (100 $pg/mm^2$); Grating Couplers (2.5 $pg/mm^2$); Surface Plasmon Resonance (10 $pg/mm^2$).

The devices and methods of the present invention employ a porous semiconductor layer as an element of their interferometric sensors. A "porous semiconductor layer" is a porous layer having a relatively consistent thickness, relatively consistent porosity and made up of a semiconducting solid that is relatively transparent. A "semiconducting" material is one having a bulk resistivity of from about 1 to about $1\times10^7$ ohms per cm.

The term "transparent" as used herein refers to the property of a material to transmit a fraction, such as at least about 20% of a suitable range of wave lengths of light from which Fabry-Perot fringes can be generated.

The term "light" is employed herein to include not only the visible portion of the electromagnetic spectrum, i.e. 350–800 nm, but also the infrared region of from say 800–3000 nm and the ultraviolet region of from about 50–350 nm. Longer and shorter wavelengths can be employed as well. The wavelengths employed can play a part in the selection of layer thickness and pore size of the porous semiconductor layer. As a general rule shorter wavelengths permit thinner layer thicknesses and smaller pore sizes while longer wavelengths permit thicker layer thicknesses and larger pose sizes.

The porous semiconductor layer can range in thickness from about 0.5 to about 30 microns with thicknesses of from about 1 or 2 to about 10 microns being preferred when visible light such as white light is employed and with thicknesses of from about 5 to about 30 microns being preferred with infrared wave lengths and thicknesses of from about 0.5 to 5 microns being preferred with ultraviolet wave lengths.

The pores (or cavities) in the porous semiconductor layers are typically sized in terms of their nominal "diameter" notwithstanding the fact that they are somewhat irregular in shape. These diameters range from about 2 nm to about 2000 nm with diameters of from about 10 to about 200 nm being preferred for visible light and 2–50 nm diameters being preferred for ultraviolet light and 100 to 2000 nm being preferred for infrared light. The surface of the solid semiconductor is flat with a substantial degree of porosity such as from about 10% to about 80% of the surface area and typically from 20 to 70% of the surface area.

The semiconducting porous layer can be formed of any semiconductor capable of being formed into the porous structure of the desired thickness and porosity. Silicon and silicon alloys are preferred semiconductors because of their amenability to the preferred galvanic etching process described herein for forming porous structures. These materials can include p-doped silicon, n-doped silicon, intrinsic (undoped) silicon, as well as alloys of these materials with, for example germanin in amounts of up to about 10% by weight as well as mixtures of these materials.

A representative device depicted in FIG. 1 is prepared from an electrochemical etch of a semiconductor such as single-crystal p-type (boron-doped) silicon wafers that produce microporous silicon that displays well-resolved Fabry-Perot fringes in its reflectometric interference spectrum. Silicon-containing (silicious) semiconductors are preferred herein, and although p-type silicon wafers are utilized herein as exemplary substrates, it is to be understood that n-type silicon and undoped, intrinsic silicon can be used, as a silicon-germanium (Si—Ge) alloy containing up to about 10 mole percent germanium, Group III element nitrides and other etchable semiconductor substrates. Exemplary semiconductor substrates and dopants are noted below.

| n dopant | p dopant |
|---|---|
| $H_2Se$ | $(CH_3)_2Zn$ |
| $H_2S$ | $(C_2H_5)_2Zn$ |
| $(CH_3)_3Sn$ | $(C_2H_5)_2Be$ |
| $(C_2H_5)_3Sn$ | $(CH_3)_2Cd$ |
| $SiH_4$ | $(\eta C_2H_5)_2Mg$ |
| $Si_2H_6$ | B |
| P | Al |
| As | Ga |
| Sb | In |

The substrate can be GaAs, Si, $Al_2O_3$, MgO, $TiO_2$, SiC, ZnO, $LiGaO_2$, $LiAlO_2$, $MgAl_2O_4$ or GaN.

Reflection of light at the top (surface) and bottom of the exemplary porous semiconductor layer results in an interference pattern that is related to the effective optical thickness (product of thickness L and refractive index n) of the film by eq. 1, $$m\lambda = 2\,nL \tag{1}$$

where m is the spectral order and $\lambda$ is the wavelength of light. Binding of an analyte to its corresponding recognition partner, immobilized on the porous silicon substrate area results in a change in refractive index of the layer medium and is detected as a corresponding shift in the interference pattern.

The refractive index, n, for the porous semiconductor in use is related to the index of the semiconductor and the index of the materials present (contents) in the pores pursuant to eq. 2

$$n = (1-P)n_{semiconductor} + Pn_{contents} \tag{2}$$

Where P=porosity of porous semiconductor layer; $n_{semiconductor}$=refractive index of semiconductor; $n_{contents}$= refractive index of the contents of the pores.

The index of refraction of the contents of the pores changes when the concentration of analyte species in the pores changes. Most commonly, the analyte (target) species is an organic species that has a refractive index that is larger than that of the semiconductor. The replacement of a species of lower index of refraction (water) by another species of higher index of refraction (analyte) would be expected to lead to an increase in the overall value for index of refraction. An increase in index should result in a shift in the interference pattern wavelengths to longer values; i.e., a bathochromic or "red" shift pursuant to equation 1. Contrarily, the observed shift in interference pattern wavelengths is opposite that which is expected; i.e., is toward shorter wavelengths exhibiting a hypsochromic or "blue" shift.

The basis for the observed wavelength blue shift is not understood with certainty. However, the observed, unexpected hypsochromic shift in wavelengths is believed to be the result of a reduction in the index of refraction of the semiconductor itself that is induced by the intimate association of the semiconductor with the bound analyte.

White light is preferred for carrying out reflectance measurements, and is used illustratively herein. The use of white light or other light in the visual spectrum can permit a determination of the presence of an analyte in a sample by visual inspection of a color change in the reflected light without the need of special apparatus. It should be understood, however, that reflected infrared (IR) and ultraviolet (UV) light canals be utilized along with an appropriate spectral measuring device.

The sensors of the present invention include the binder molecule (also referred to as the "recognition partner") for the analyte and the like that is bound to or otherwise intimately associated with the porous semiconductor surface. This intimate association can be accomplished by any approach that leads to the tethering of the binder molecule to the semiconductor. This includes without limitation covalently bonding the binder molecule to the semiconductor, ionically associating the binder molecule to the substrate, adsorbing the binder molecule onto the surface of the semiconductor, or the like. Such association can also include covalently attaching the binder molecule to another moiety, which in turn is covalently bonded to the semiconductor, bonding the target molecule via hybridization or another biological association mechanism to another moiety with is coupled to the semiconductor.

The binding of an analyte to its corresponding recognition partner, immobilized on the porous silicon substrate, results in a change in refractive index of the layer medium and is detected as a corresponding shift in the interference pattern. Recognition partners or binding compounds can be peptides, small molecules (molecular weight of less than about 500), metal ions and their preferably organic binding ligands, antibodies, antigens, DNA, RNA or enzymes. More broadly, a recognition partner can be any receptor of an acceptor molecule that can be adsorbed by the substrate and binds to a ligand provided by of another molecule or ion.

More specifically, the Examples that follow illustrate use of two different single strands of binder DNA (SEQ ID NOs:1 and 2) bound to the porous silicon substrate, and two different single DNA strands (SEQ ID NOs:3 and 4, respectively) as analyte (Examples 1 and 3). Example 4 illustrates the use of a biotin-bound porous silicon substrate with strepavidin, as well as biotnylated anti-mouse antibodies that were used to analyze for mouse-anti-digoxigenin, and those antibodies were then used to assay for the presence of digoxigenin. Further exemplary binding pairs include so-called polypeptide P-62 (SEQ ID NO:5) of U.S. Re. 33,897 (1992), whose disclosures are incorporated by reference, with human antibodies to the Epstein-Barr nuclear antigen (EBNA) as analyte; monoclonal antibodies ATCC HB 8742 or HB 8746 that immunoreact with human apolipoprotein B-100 as analyte, or monoclonal antibodies ATCC HB 9200 or HB 9201 that immunoreact with human apolipoprotein A-I as analyte as are described in U.S. Pat. No. 4,828,986, whose disclosures are incorporated by reference; and the several deposited monoclonal antibodies listed at column 13 of U.S. Pat. No. 5,281,710, and their listed binding partners as analyte, which disclosures are incorporated by reference.

Electrochemical etching of Si can generate a thin (approximately 1–10 $\mu$m) layer of porous Si on the silicon substrate with cavities of about 10 nm to about 200 nm in diameter, providing a large surface area for biomolecular interaction inside the porous Si layer. The porous films are uniform and sufficiently transparent to display Fabry-Perot fringes in their optical reflection spectrum.

More particularly, a porous Si substrate is prepared by an electrochemical etch of a polished (100)-oriented p-type silicon (B-doped 3 Ohm-cm resistivity) wafer. The etching solution is prepared by adding an equal volume of pure ethanol to an aqueous solution of HF (48% by weight). The etching cell is constructed of Teflon® and is open to air.

Si wafers are cut into squares with a diamond scribe and mounted in the bottom of the Teflon® cell with an O-ring seal, exposing 0.3 cm$^2$ of the Si surface. Electrical contact is made to the back side of the Si wafer with a strip of heavy aluminum foil, such as heavy duty household aluminum foil. A loop of platinum wire is used as a counter-electrode. The exposed Si face can be illuminated with light from a tungsten lamp for the duration of the etch in order to enhance the optical properties of the films. Etching is illustratively carried out as a 2-electrode galvanostatic operation at an anodic current density of 5 mA/cm$^2$ for 33 minutes. After etching, the samples are rinsed in ethanol and dried under a stream of N$_2$. Scanning electron microscopy and atomic force microscopy showed that porous silicon films so prepared were about 5–10 microns thick and contained an average of 200 nm diameter pores.

The porous semiconductor so prepared was modified by oxidation with bromine gas in an evacuated chamber for one hour, followed by hydrolysis in air. The molecular recognition elements were then attached to the resulting silicon dioxide surface using conventional techniques.

The sensors of this invention can be employed as discrete, independent units. Multiple sensors can also be arrayed together. Where multiple sensors are desired to be arrayed together, a plurality of porous areas can be etched on to the surface of a single semiconductor substrate in much the same way as microchip patterns are prepared A plurality of separate porous areas can also be combined to form a desired array.

An array of sensors can make it possible to have a plurality of concentrations of a single binder molecule on a single plate so as to provide a "dose-response curve" for a particular analyte. Multiple sensors also can make it possible to have a plurality of different binder molecules on the same plate so as to make multiple screenings in a single test.

A sensor having a plurality of individual porous areas can be analogized to a multi-well microtiter plate, and can contain the same or different associated binder compound at any desired porous area so that the same or a different binding assay can be carried out on each porous area. The individual binder compound-porous areas are then illuminated. Binding studies with analytes are then carried out for those areas, followed by reillumination. Binding results are obtained in a manner similar to that used for the individual porous areas exemplified herein.

Spectral Measurement

To measure optical interference spectra, a Princeton Instruments CCD photodetector/Acton research 0.25 m monochrometer, fitted with a fiber optic and microscope objective lens to permit detection from small (<1 mm$^2$) sample areas was used for the studies described here, but similar equipment is well-known and can be used instead. The white light source for the experiments was a low intensity krypton, tungston or other incandescent bulb. A linear polarizing filter was used to enhance the appearance of the interference spectra.

The substrate can be pre-treated with a chemical receptor (binder compound) species (such as an antibody) to provide chemical specificity. For gas measurements, the sample was mounted in a Pyrex® dosing chamber and exposed to the gaseous analyte of interest. For liquid-phase measurements, as in an aqueous medium, a Teflon® and O-ring cell similar to the cell employed in etching the porous layer was used. Measurements have also been taken using a liquid flow-through chamber equipped with glass or plastic window.

The fringe pattern can be changed by replacing the air or liquid in the pores with a material of differing refractive index. The shift in fringe maxima corresponds to a change in the average refractive index of the thin film medium. Solution of the simultaneous equations provided by measurement of the fringe spacing provides a quantitative measurement that can be related to the analyte concentration. Chemical specificity can be introduced by incorporating or chemically bonding molecular recognition agents such as peptides, antibodies, antigens, single- or double-strand DNA or RNA, enzymes, a metal ion-binding ligand and the like onto the inner surfaces of the porous Si film. Control measurements can be performed on a similar sample that does not contain the molecular recognition elements. Further details as to the preparation of a porous silicon substrate and apparatus used for spectral measurements can be found in U.S. Pat. No. 5,338,415, whose disclosures are incorporated by reference.

Thus, one aspect of the invention contemplates a process for detecting a analyte molecule such as an organic molecule analyte. In accordance with that process, a porous silicon substrate is provided and prepared, and that prepared substrate is provided and contacted with a binder compound to form a binder compound-bound substrate. The wavelength maximum of the Fabry-Perot fringes is determined upon illumination of the binder compound-bound substrate. That binder compound-bound substrate is thereafter contacted with a sample to be assayed that may contain an analyte that is an organic molecule that binds to the binder compound of the substrate. When the desired analyte is present in the sample, in distilled water or various buffer solutions that ligand binds to the binder compound to form a ligand-bound substrate. The contact between the sample and binder compound-bound substrate can be maintained for a few seconds to several hours, as desired to form the ligand-bound substrate. When the substrate is thereafter reilluminated with the same light source, a shift in the wavelength maximum of the Fabry-Perot fringes from that previously determined indicates the detection and therefore presence of the analyte in the sample.

Without committing to any particular theory in support of the subject invention, it is believed that the unique sensitivity of the system involves selective incorporation or concentration of an analyte such as an illustrative organic analyte in the porous Si layer to modify the refractive index by two effects: increase of the average refractive index of the medium in the pores by replacing water (refractive index 1.33) with organic matter (refractive index typically 1.45), and also decrease of the refractive index of the Si by modifying the carrier concentration in the semiconductor. A net increase in refractive index is expected to shift the interference spectrum to longer wavelengths, whereas a decrease in index is expected to shift the spectrum to shorter wavelengths. Without exception, a shift to shorter wavelengths in such cases has been observed, indicating that the induced change in the semiconductor overwhelms the refractive index change occurring in the solution phase.

Each of Examples 1–3 was carried out in 1.0 M aqueous NaCl at 25° C., whereas Examples 4 and 5 were carried out in 0.5 M NaCl.

EXAMPLE 1

Binder DNA oligonucleotide-derivatized porous silicon films were employed to test the selectivity and limits of detection of a contemplated sensor. For attachment of DNA, a trimethoxy-3-bromoacetamido-propylsilane linker was synthesized by reaction of bromoacetic acid with trimethoxy-(3-aminopropyl)silane in the presence of 1-(3-dimethylaminopropyl)-3-ethylcarbodiimide-hydrochloride in methylene chloride as solvent The linker product was purified by column chromatography on silica gel. The oxidized porous silicon samples were then contacted with a toluene solution of the linker for 2 hours. The resulting linker-bound substrate was thoroughly rinsed with pure toluene and methylene chloride, and dried for about 18 hours under reduced pressure.

HPLC-Purified 5'-phopsphorothiate oligonucleotides (DNA-A and DNA-B, illustrated hereinafter) were separately dissolved at about 50 nmol in a solution of 1:1:0.2; water/DMF/5%NaHCO$_3$ and admixed with the linker-bound porous semiconductor substrate for about 2 hours. The presence of the DNA-modification on the porous surface of the resulting binder compound-bound substrate was confirmed by FTIR spectroscopy.

Figure 2:
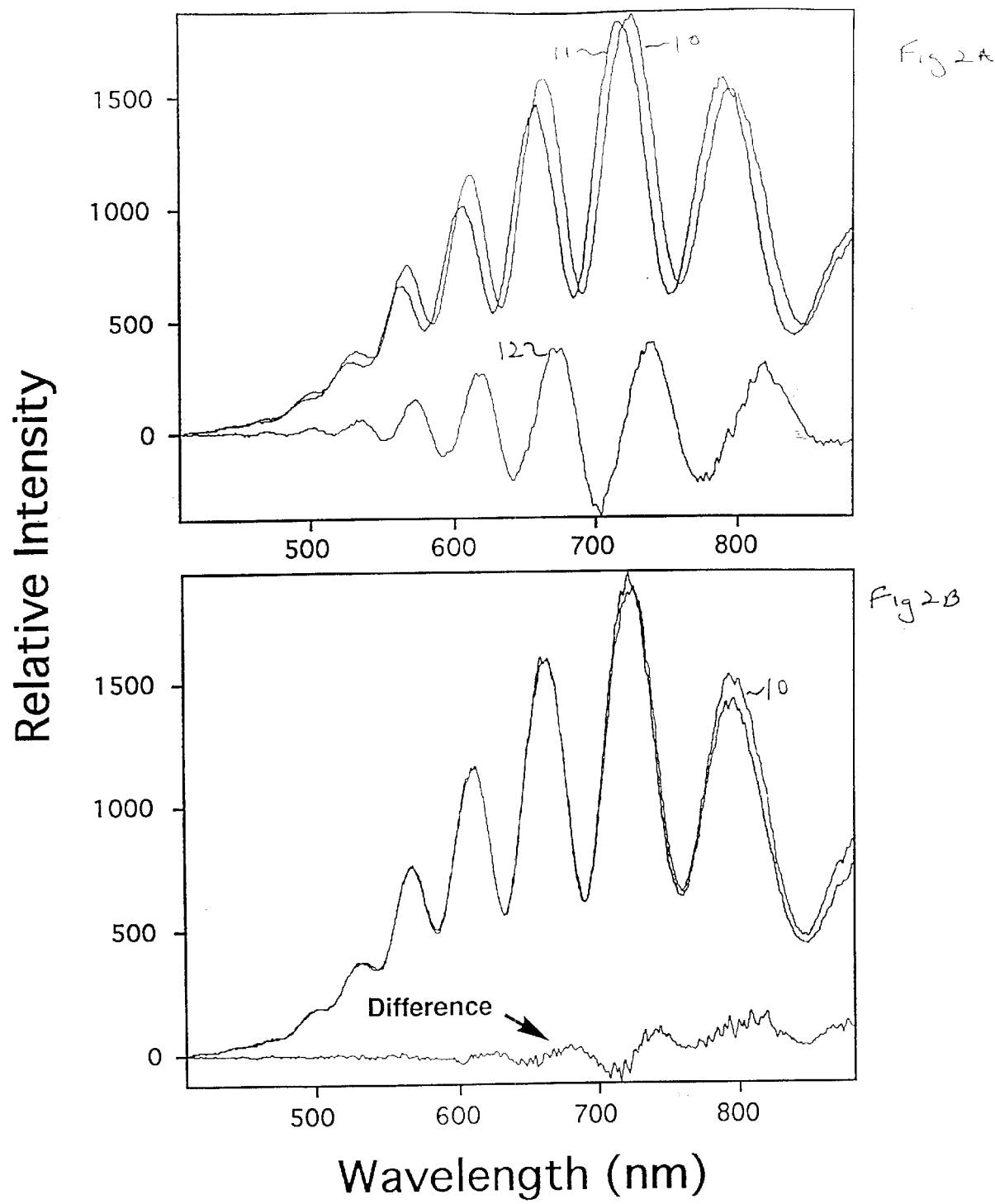
FIGS. 2A and 2B are interferometric reflectance spectra of DNA-modified porous Si layers.

In the presence of complementary analyte DNA sequences (DNA concentrations ranging from $2\times10^{-15}$ M to $2\times10^{-6}$ M) pronounced wavelength shifts in the interference pattern of the porous silicon films were observed (FIG. 2). Under similar conditions but in the presence of noncomplementary DNA sequences, no significant shift in the wavelength of the interference fringe pattern was detected-only minor amplitude fluctuations were observed.

Specifically, measurements were made of two DNA sequences:

DNA-A: 5'-pGC CAG AAC CCA GTA GT-3'    SEQ ID NO:1 and

DNA-B: 5'-CCG GAO AGA AGC AGA A-3'    SEQ ID NO:2, and corresponding complementary strands [(DNA-A' (SEQ ID NO:3) and DNA-B' (SEQ ID NO:4)]. For clarity, only one set of data are shown.

In FIG. 2A, the Fabry-Perot fringes 10 from a porous Si surface derivatized with DNA-A are shown to shift to shorter wavelength 11 upon exposure to a $2\times10^{-12}$ M solution of DNA-A' (the complementary sequence of DNA-A) in 1 M NaCl (aq). The net change in effective optical thickness (from 7,986 to 7,925 nm) upon DNA-A' recognition is represented by the difference 12 between the two interference spectra.

EXAMPLE 2

FIG. 2B represents a control for Example 1, showing the Fabry-Perot fringes 10a of a DNA-A derivatized porous Si surface before and after exposure to a $2\times10^{-12}$ M solution of DNA-B (non-complementary sequence) in 1 M NaCl(aq). No wavelength shift was observed up to the measured concentration of $10^{-9}$ M of DNA-B.

EXAMPLE 3

Figure 3:
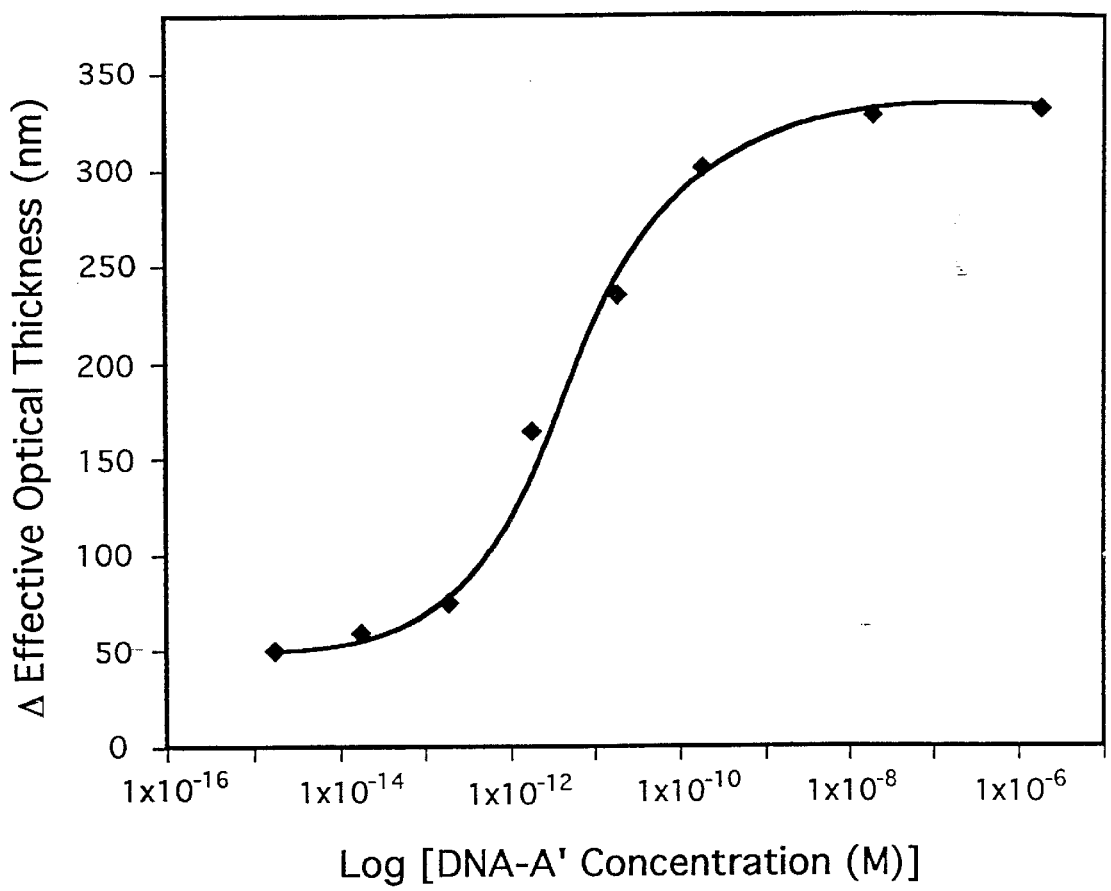
FIG. 3 shows the change in effective optical thickness in a DNA-A-modified porous Si layer as a function of DNA-A' concentration.

Fluorescence spectroscopy was used to independently investigate the surface coverage of immobilized DNA on porous Si and the rate of analyte diffusion into the Si substrate for the purposes of comparison with the subject invention. Solutions of fluorescein-labeled analyte complementary DNA oligonucleotides were placed in fluorescence cuvettes and the binder DNA-derivatized porous Si substrate was then added to the cell without stirring. At lowest DNA concentrations employed in the study, the fluorescence intensity of the samples decreased to an asymptotic limit in 40 min (similar equilibration times were observed in the interferometric measurements described above) (FIG. 3). The data indicate $1.1\times10^{-12}$ mol of bound DNA in a 1 mm$^2$ porous Si substrate (calculated from standardized fluorescence titration curves). The data obtained from the reflectometric interference measurements also provided a similar coverage number.

EXAMPLE 4

The subject invention was used to sense multiple layers of biomolecular interactions (cascade sensing) and small molecule detection. A linker with attached biotin was prepared by reaction of Iodoacetyl-LC-biotin (Pierce Biochemicals) with 3-mercaptopropyl-trimethoxysilane (Aldrich Chemicals) in dimethylformamide (DMF). After purification, the biotinylated linker was dissolved in ethanol or DMF and the oxidized, porous semiconductor was immersed in the solution for 12 hours. The sample was then rinsed thoroughly with ethanol, and dried under a stream of nitrogen to provide a binder compound-bound substrate.

Exposure of a biotinylated (binder) porous Si substrate to a $5 \times 10^7$ M analyte streptavidin solution resulted in a large blue-shift of the interference fringes, corresponding to a decrease in the measured effective optical thickness from 12,507–11,994 nm (the lowest streptavidin concentration employed was $10^{-14}$ M) (FIG. 4A). Control studies performed by exposing a biotinylated porous Si substrate to inactivated streptavidin (streptavidin pre-saturated with biotin) did not display perceptible shifts in interference pattern.

The biotin-streptavidin monolayer surface was contacted with aqueous $10^{-8}$ M biotinylated anti-mouse IgG (from goat IgG). Binding of this secondary antibody to the surface was indicated by a decrease in effective optical thickness of the monolayer from 11,997 to 11,767 (lowest concentration employed with a detectable signal was $10^{-12}$ M) (FIG. 4B). Treatment of the secondary antibody sample with anti-digoxigenin (mouse IgG) at a concentration of $10^{-8}$ M caused a further decrease in the effective optical thickness of the monolayer from 11,706 to 11,525 nm (FIG. 4C). The interaction of digoxigenin ($10^{-6}$ M), a steroid with molecular weight of 392, with the anti-digoxigenin IgG-bound porous Si surface was also detected with a decrease of the effective optical thickness from 11,508 to 11,346 nm (FIG. 4D).

EXAMPLE 5

To rule out the possibility of nonspecific interaction, a non-biotinylated surface was subjected to the same solution, and conditions as described in Example 4. No measurable change in the effective optical thickness was observed on treatment with streptavidin, secondary antibody, primary antibody, and digoxigenin. Detection of the relatively small biotin molecule (MW=244) at concentrations as low as $10^{-12}$ M has also been demonstrated using biotin-streptavidin-modified porous Si.

Although the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

---

What is claimed is:

1. A reflective sensor for an analyte comprising a semiconductor substrate having a porous surface area, said porous surface area having a coating consisting essentially of an organic binder compound thereon, said organic binder compound binding selectively with said analyte and shifting the wavelength of the substrate surface area.

2. The reflective sensor of claim 1 wherein said semiconductor is a silicious semiconductor.

3. The sensor of claim 2 wherein said silicious semiconductor is selected from the group consisting of intrinsic silicon, p-doped silicon, n-doped silicon, alloys of silicon and mixtures thereof.

4. The sensor of claim 3 wherein said alloys of silicon comprise silicon alloyed with up to about 10% by weight of germanium.

5. The reflective sensor of claim 1 wherein said binder compound is selected from the group consisting of peptides, antibodies, antigens, DNA, RNA, ligands that bind to metal ions and enzymes.

6. A reflective sensor for an analyte comprising a semiconductor substrate comprising a silicon alloy with up to about 10% by weight of germanium and having a porous surface area, said porous surface area having an organic binder compound thereon, said binder compound binding selectively with said analyte.

* * * * *